US005939229A

United States Patent [19]
Robbins

[11] Patent Number: 5,939,229
[45] Date of Patent: Aug. 17, 1999

[54] METHOD FOR DETERMINING CHEMICAL CROSS TALK OR ISOTOPIC SCRAMBLING INDUCED BY ANALYTICAL PROCEDURES

[75] Inventor: Ronny C. Robbins, Balto, Md.

[73] Assignee: The United States of America as represented by the Secretary of the Army, Washington, D.C.

[21] Appl. No.: 08/806,010

[22] Filed: Feb. 25, 1997

[51] Int. Cl.$^6$ .......................... G01N 23/00; G01N 23/225
[52] U.S. Cl. ................................. 430/57; 436/56; 436/173
[58] Field of Search ................................ 436/57, 173, 59, 436/56

[56] References Cited

PUBLICATIONS

Knesaurek, Biosis 95:451015.

Primary Examiner—Lyle A. Alexander
Attorney, Agent, or Firm—Ulysses J. Biffoni; Edward L. Stolarun

[57] ABSTRACT

Methods and compositions for determining the amount of chemical cross talk or isotopic scrambling, induced by an analytical procedure on a test sample using a reference standard composition containing a predetermined ratio of isotopes is disclosed. The method includes subjecting a reference sample which comprises a predetermined ratio of labeled isotopes to an analytical procedure; determining the degree of isotopic scrambling in the reference sample, subjecting a test sample to the identical analytical procedure; the degree of isotopic scrambling caused by the analytical procedure to the reference sample provides an indication of the presence of chemical cross-talk caused by the analytical procedure on the test sample. In preferred aspects, the cross talk is determined using mass spectral analysis and the reference sample comprises an algae mixture having a predetermined ratio of carbon-12 to carbon-13 isotopes.

8 Claims, No Drawings

METHOD FOR DETERMINING CHEMICAL CROSS TALK OR ISOTOPIC SCRAMBLING INDUCED BY ANALYTICAL PROCEDURES

GOVERNMENT INTEREST

The invention described herein may be manufactured, licensed, and used by or for the U.S. Government.

BACKGROUND OF THE INVENTION

1. Field of the Invention

The present invention relates to methods for improving the accuracy and precision of data obtained from analytical procedures. In particular, the invention relates to compositions and methods of measuring levels of chemical noise and/or chemical cross talk induced in a test sample being analyzed with a biodetector.

2. Description of the Prior Art

"Chemical noise" is a term of art which suggests the presence of unwanted chemicals generated through means such as isotopic scrambling which interfere with the detection of a substance or chemical of interest from a sample. Chemical noise arises from naturally-occurring chemicals found in samples that are being analyzed. Lead, cyanide, DDT, PCB's, and the like occur in practically everything if one looks at a sample on a molecule-by-molecule basis. This naturally-occurring chemical background material can interfere with the accurate analysis of samples, especially when it is necessary to detect and identify the presence of minute quantities of an agent in a sample. Samples can also pick up chemicals from the background and introduce "noise" during analytical procedures. For example, if the amount of chemical noise is significant, the results obtained from analyzing a given sample can be skewed by orders of magnitude and provide one with false positive and/or false negative results.

An example of chemical cross-talk is illustrated below. A certain chemical reaction may involve methane ($CH_4$). If one were to replace the hydrogen with deuterium and the carbon with carbon-13, the chemical formula would be $^{13}C^2H_4$, for labeled methane. However, if one were to then mix the unlabeled methane with the labeled methane in a reaction vessel and later did an analysis, the following products might be found:

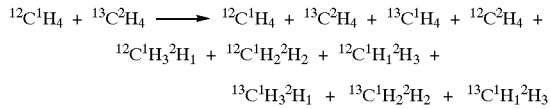

With the labeled methane, one can determine that this type of atomic exchange was occurring. More importantly, one could determine that there was chemical noise or cross-talk involved in the reaction being monitored and measure it.

In view of this phenomenon, it becomes important, especially when accurate readings of samples are required, that biodetectors include some indication or measure of the magnitude of chemical noise and/or chemical cross-talk present in a sample during analysis in a biodetector detection system.

Recently, the military has adopted techniques where biodetectors are used to determine the presence of biological warfare materials in a sample. Given the highly lethal nature of such materials, accurate measurements are essential. Interference caused by chemical noise could cause military personnel to be unnecessarily exposed to hazardous materials or take unnecessary precautions. Thus, the biodetectors employed must be able to account for any chemical noise and/or cross-talk which would skew the analysis results.

Mass Spectrometry (MS) has long been used to study simple organic compounds. Peptides, proteins, and other biomolecules were often more difficult to analyze with MS. The molecules were simply too big and fragile to survive the high temperatures required to get samples into the gas phase for MS analysis. This problem, however, has been recently solved by the introduction of desorption techniques such as fast atom bombardment, Electrospray Ionization (ESI) and Matrix-Assisted Laser Desorption/Ionization (MALDI). Thus, mass spectrometry is now being used as an analytical procedure in biodetection applications.

Mass spectrometry can also be used to efficiently determine isotope ratios (the concentration of rare isotope to the concentration of total element) as low as one part per billion (ppb) in microgram to nanogram samples. Contamination of a sample with an isotope or otherwise unwanted chemical can occur during sample preparation and during the analytical methods used to analyze the sample. The isotope can be incorporated in the sample from the surrounding matrix (the environment at large) or due to radiation or other in situ production.

Isotopic labeling of chemicals has been traditionally used in mass spectrometry to profile reaction mechanisms. However, most studies have been limited to compounds of relatively low molecular weight. (See above reaction scheme concerning methane). For very large and/or complex mixtures, chemical exchange of labeled nuclei might occur which would, of course, limit the usefulness or value of the data obtained.

SUMMARY OF THE INVENTION

In view of the foregoing, it is therefore an object of the present invention to provide cost effective compositions and methods which are useful in determining the amount of chemical cross-talk or chemical noise present in or generated by an analytical procedure.

It is a further object of the invention to provide a method of identifying whether the steps of a given analytical procedure impart chemical cross-talk to a test sample undergoing that analytical procedure.

In one aspect of the invention, these and other objects of the invention are achieved by a method of determining the presence of chemical cross-talk conveyed by an analytical procedure to a test sample. The method includes:

subjecting a reference sample which comprises a predetermined ratio of labeled isotopes to said analytical procedure;

determining the degree of isotopic scrambling in the reference sample, and then subjecting a test sample to the same analytical procedure; so that the degree of isotopic scrambling caused by the analytical procedure to the reference sample provides an indication of the presence of chemical cross-talk caused or conveyed by the analytical procedure to the test sample.

In another aspect of the invention there is provided a composition for use in determining the amount of isotopic scrambling caused by an analytical procedure. The composition includes a predetermined ratio of isotopes.

In preferred aspects of the invention, the reference sample or composition for use in determining the amount of cross-talk or isotopic scrambling contains about a 50—50 ratio of labeled and non-labeled isotopes. One preferred mixture of isotopes is a 50—50 ratio of carbon-13 and carbon-12.

As a result of the invention there are provided methods and compositions which allow the artisan the ability to identify and, if desired, quantify the amount of chemical cross-talk generated by an analytical procedure. The methods and compositions are relatively inexpensive to use and thus allow one to obtain a more precise analytical result at a reasonably low cost. Moreover the artisan is alerted to the fact that the results provided by a given analytical procedure contain a degree of imprecision and that the imprecision is caused by the analytical procedure itself.

DETAILED DESCRIPTION OF THE PREFERRED EMBODIMENT

The present invention provides a method of determining the presence of chemical cross-talk conveyed by an analytical procedure to a test sample. This method thus addresses a shortcoming known to artisans using biodetectors in field operations or laboratories. The artisan is now able to determine and/or confirm the presence of cross-talk introduced into a sample unknown, hereinafter the test sample, by a necessary analytical procedure. In the past, it was difficult and often impractical to make such determinations immediately prior to conducting the procedure. For example, the present invention allows the artisan to determine whether chemical exchange or isotopic scrambling is occurring as a result of an analytical procedure such as pyrolysis.

In a preferred embodiment, the method includes the steps of:

subjecting a reference sample containing a predetermined ratio of labeled isotopes to the analytical procedure;

determining the degree of isotopic scrambling in the reference sample, subjecting a test sample to the same analytical procedure;

wherein the degree of isotopic scrambling detected in the reference sample caused by the analytical procedure under consideration provides an indication of the chemical cross-talk caused by the analytical procedure on the test sample.

Preferably, the degree of isotopic scrambling is determined using curie point mass spectra analysis of the reference sample.

The reference sample used in carrying out the present invention includes a predetermined ratio of isotopes. This enables the artisan to conduct the analytical procedure with the knowledge that mass spectra of the reference sample should be predictable, i.e. corresponding to the predetermined ratio. If the mass spectra does not confirm the presence of the predetermined ratio, then the artisan can fairly assume the procedure conveys chemical cross talk to not only the reference sample but also any test sample or sample unknown.

The predetermined ratio of isotopes in the reference sample is selected so that maximum sensitivity can be achieved for determining isotopic scrambling. In this regard, therefore, the predetermined ratio of isotopes included in the reference standard can be, for example, about 1:4, preferably about 1:2, and most preferably about 1:1.

One particularly preferred reference sample includes an approximately 50/50 mix of carbon-12 and carbon-13 algae. This composition provides several advantages when used in the context of the invention described herein when there is interest in determining the presence of cross-talk conveyed by biodetectors such as chemical biological mass spectrometers which are used by military personnel to test for the presence of biological or chemical warfare agents. Furthermore, the process of the present invention can be used with any biodetection system. The mixture is relatively low cost and the ingredients can be purchased commercially i.e. from MSD isotopes (St. Louis, Mo.) or made in a laboratory using known techniques. When pure carbon-13 labeled algae is mixed with carbon-12 algae, and reactions are carried out on the mixture, i.e., using a biodetector, one can look at the reaction products and determine the degree that the carbon-12 labeled algae has interacted with its chemical background, the carbon-13 labeled algae, using C-12 to C-13 ratio of each ion in mass spectrum using a high resolution mass spectrometer. The chemical products made as a result of the chemical reactions caused by the analytical procedure will show, via mass spectrometry analysis, whether and how much isotopic scrambling occurred.

In view of the foregoing, the isotopes included in the reference sample preferably comprise carbon-13 and carbon-12. Alternatively, the isotopes preferably comprise deuterium and hydrogen.

In another aspect of the invention there is provided a composition for use in determining the amount of isotopic scrambling caused by an analytical procedure. The composition, as described above with regard to the reference standard sample thus includes a predetermined ratio of isotopes which allow an artisan to conduct an analytical procedure knowing what the mass spectra data should be if there is no scrambling and, if there is scrambling, the information necessary to quantify the degree of isotopic scrambling.

Thus, the composition of the invention preferably has an isotope ratio of about 1:4, more preferably of about 1:2 and most preferably of about 1:1. As stated above, the preferred compositions include carbon-13 and carbon-12 and in another embodiment, comprise deuterium and hydrogen.

EXAMPLES

The following non-limiting examples serve to illustrate the invention.

EXAMPLE 1

In order to demonstrate the method of the present invention, two test tubes were prepared to separately contain a target or sample unknown in test tube A and a reference sample in test tube B designed to contain an approximately equal amount (i.e. 50/50) of carbon-12 algae and carbon-13 algae. The carbon-12 and carbon-13 portion of the mixture of algae is approximately at least about 98% pure. In order to determine whether a particular procedure would convey cross-talk to a sample unknown, the procedure was carried out using a reference sample which contained the algae mixture of known ratio of isotopes. In this particular case, the procedure was carried out on both test tube A (unknown or target sample) and test tube B (algae mixture) simultaneously. If desired, the artisan could subject reference sample-containing test tube to the procedure under consideration and thereafter subject the test tube containing the sample unknown to the procedure.

|  | Test tube A | Test tube B |
|---|---|---|
| Contains | Fungus (Target Sample) | Carbon-12 & Carbon-13 Algae 50/50% Mix (Reference Sample) |

Weight of each Sample=0.1 grams

Each of the samples were subjected to the following analytical procedure:

| Step | Test tube A (Fungus) | Test tube B (Reference Algae) | Procedure |
|---|---|---|---|
| step 1 | add 1 ml water | add 1 ml water | mix and stir |
| step 2 | add 1 ml methanol | add 1 ml methanol | mix and stir |
| step 3 | wait 10 min | wait 10 min | let stand |
| step 4 | expose solution to Ultrasonic Radiation | expose solution to Ultrasonic Radiation | mix and stir Irradiate for 10 minutes |
| step 5 | filter out solid fungus | filter out solid algae | filter and dry |
| step 6 | Coat Sample onto Curie Point Wire | Coat Sample onto Curie Point Wire | Take the Curie Point Mass Spectra |

When the artisan looks at the mass spectra data for the algae in test tube B, the reference sample-containing test tube, he is faced with two possibilities.

Case #1—mass spectra peaks correspond to 100% Carbon-12 or 100% Carbon-13 i.e. all carbons contained in any one peak are all Carbon-12 atoms or all carbons contained in any one peak are Carbon-13 atoms. In this case, the conclusion would be that the procedure does not induce any chemical crosstalk in the algae mixture in test tube B. Consequently, it can be deduced that the procedure did not convey any chemical cross talk to the sample unknown in test tube A.

Case #2—Alternatively, the mass spectra peaks found after the procedure may correspond to less than 100% Carbon-12 or 100% Carbon-13 for the reference sample. The mass spectra peaks may correspond to the values set forth in Table 1, below.

TABLE 1

| CARBON-12 PERCENT IN MASS ION | CARBON-13 PERCENT IN IN MASS ION | TOTAL PERCENT | DEGREE OF CHEMICAL CROSS TALK |
|---|---|---|---|
| 0% | 100% | 100% | None |
| 10% | 90% | 100% | small |
| 20% | 80% | 100% | large |
| 50% | 50% | 100% | great |
| 80% | 20% | 100% | large |
| 90% | 10% | 100% | small |
| 100% | 0% | 100% | None |

Given the above range of possibilities, the artisan can infer the degree of chemical cross talk one is likely to experience using the selected analytical procedure on the sample unknown in test tube A, which in this case contains a fungus, by the mass spectral data of the 50/50 mixture of carbon-12/carbon-13 algae contained in test tube B as the reference sample which has undergone the identical analytical procedure.

If the mass spectral data of peaks in test tube B corresponds to a 45%/55% peak ratio, i.e. they correspond to a 45%/55% carbon-12 to carbon-13 ratio, then the degree of chemical cross talk due to the analytical procedure can be determined. By looking in Table 1, this ratio is closest to a 50%/50% ratio which indicates a great degree of chemical cross talk in the reference test tube B mixture. Thus, it is inferred that test tube A-containing the unknown fungus also would contain a high degree of chemical cross talk as a result of the procedure.

EXAMPLE 2

In this example, the method of the present invention was used to assist in the determination of anthrax present in ambient air while at the same time allowing the technician to account for any chemical cross-talk which may be present as a result of conducting the analysis using pyrolysis mass spectrometry after air collection of the samples using a chemical biological mass spectrometer (CBMS) obtained from Bruker Analytical Systems, Inc. Billenca, Mass. Military units often need to monitor air samples in order to determine the presence of chemical or biological warfare agents such as anthrax which may have been released and therefore are present in the ambient atmosphere. The technician also needs to determine the signal to (chemical) noise ratio so that the confidence level of the data obtained as a result of carrying out the detection test can be determined.

Briefly stated, two pyrolysis mass spec. analyses were carried out, one using samples collected from air and the other using samples based on a 50/50 mixture of C-12 and C-13 algae. Although the example was carried out by performing the mass spectra analyses sequentially, it will be understood that the two tests can also be carried out in parallel if desired.

In each case, the samples collected from ambient air through the impactor nozzles of the CBMS, collected on the quartz wool and were heated with IR radiation until pyrolysis occurred. The pyrolysis products from the algae obtained from the air were sent to the CBMS for analysis. The data provided by the CBMS analysis indicated that there was no anthrax found in the ambient atmosphere. This result was verified using standard microbiological culturing techniques. However, in order to assess the confidence the technician has in the results, the signal to chemical noise ratio was calculated using the pyrolysis products obtained with the C-12-C-13 algae mixture.

The pyrolysis products obtained using the 50/50 mixture of C-12 and C-13 labeled algae were split. A portion undergoing the same CBMS analysis described above and a separate portion was sent to undergo high resolution mass spectrometry in order to determine the isotope ratio of the pyrolysis products. In this case, it was determined that the chemical noise was very low, <about 1%. Mass spectrum peaks containing carbon atoms were 100% carbon-12's or 100% carbon-13's. If there was a high level of chemical cross talk, several peaks would have been observed, one peak for each statistical ratio of carbon-12 to carbon-13 atoms.

From the foregoing, it was determined that the analytical procedure for determining the presence of anthrax induced only a slight degree of cross-talk to the test samples. Consequently, the technician has a high level of confidence in the data obtained as a result of carrying out the analytical procedure and that the amount of chemical cross talk has been minimized by the procedure.

While the invention has been described in connection with preferred embodiments, it will be understood that it is not intended to limit the invention to those embodiments. On the contrary, it is intended to cover all alternatives, modifications and/or equivalents as may be included within the spirit and scope of the invention defined in the appended claims.

What is claimed is:

1. A method of determining the presence of chemical cross-talk induced by an analytical procedure on a test sample, comprising:

subjecting a reference sample which comprises a predetermined ratio of labeled isotopes to said analytical procedure to obtain an output result indicative of a detected ratio of said isotopes determining the degree of cross-talk in the output result resulting from isotopic scrambling in said reference sample by comparing the predetermined ratio to said ratio;

subjecting a test sample to said analytical procedure to obtain another output result; and compensating said another output result based upon the determined degree of cross-talk resulting from isotopic scrambling.

2. The method of claim 1, wherein said determining step is carried out using mass spectra analysis.

3. The method of claim 2, wherein said mass spectra analysis comprises determining the curie point mass spectra of said reference sample.

4. The method of claim 1, wherein there are two isotopes and said predetermined ratio of said isotopes is about 1:4.

5. The method of claim 4, wherein said predetermined ratio of said isotopes is about 1:2.

6. The method of claim 5, wherein said predetermined ratio of said isotopes is about 1:1.

7. The method of claim 1, wherein said isotopes comprise carbon-13 and carbon-12.

8. The method of claim 1, wherein said isotopes comprise deuteruim and hydrogen.

* * * * *